United States Patent [19]

Marque

[11] Patent Number: 5,171,206
[45] Date of Patent: Dec. 15, 1992

[54] OPTIMAL CENTRIFUGAL SEPARATION

[75] Inventor: Jeffrey J. Marque, San Mateo, Calif.

[73] Assignee: Beckman Instruments, Inc., Fullerton, Calif.

[21] Appl. No.: 742,095

[22] Filed: Aug. 2, 1991

Related U.S. Application Data

[63] Continuation of Ser. No. 492,709.

[51] Int. Cl.$^5$ .................... G01M 19/00; G05B 13/04; G06F 15/46
[52] U.S. Cl. ..................... 494/37; 364/502; 494/7; 494/10; 494/11
[58] Field of Search ................ 494/37, 10, 11, 7, 1, 494/85, 16; 422/72, 100, 102; 210/781, 782; 388/810; 364/578, 502

[56] References Cited

U.S. PATENT DOCUMENTS

| | | | |
|---|---|---|---|
| 3,737,096 | 6/1973 | Jones et al. | 494/12 X |
| 4,244,513 | 1/1981 | Fayer et al. | 494/10 |
| 4,285,810 | 8/1981 | Kirkland et al. | 364/502 X |
| 4,941,868 | 7/1990 | Chulay et al. | 494/37 |
| 4,968,295 | 11/1990 | Neumann | 364/502 X |
| 5,033,012 | 7/1991 | Wohld | 364/551.01 |
| 5,113,350 | 5/1992 | Sargent | 364/502 X |

FOREIGN PATENT DOCUMENTS

| | | |
|---|---|---|
| 0344453 | 6/1989 | European Pat. Off. . |
| 2500629 | 8/1982 | France . |

OTHER PUBLICATIONS

Patent Abstracts of Japan: vol. 7, No. 286 (P-244) (1431) Dec. 21, 1983 and JP-A-58 160 843 (Horiba Seisakusho) Sep. 24, 1983.

"Equilibrium Sedimentation of Macromolecules and Viruses in a Density Gradient"; vol. 20 1962; pp. 372-385.

Garger, S. J. et al.; "Rapid Purification of Plasmid DNA By a Single Centrifugation in a Two-Step Cesium Chloride-Ethidium Bromide Gradient", *Biochemical and Biophysical Research Communications* (Dec. 1983) vol. 117, No. 3, pp. 835-842.

Sartory, W. K., et al.; "Simulation of Gradient and Band Propagation in the Centrifuge"; *Biophysical Chemistry* 5 (1976) pp. 107-135.

Steensgaard, et al.; "Computer Simulation of Density--Gradient Centrifugation"; *Subcellular Biochemistry* vol. 6, pp. 117-141, Copy-Sep. 15, 1988, Legal Dept.

*Primary Examiner*—Daniel M. Yasich
*Attorney, Agent, or Firm*—William H. May; Paul R. Harder; Wen Liu

[57] ABSTRACT

Method and apparatus for controlling the angular velocity of a centrifuge tube containing a solute and a solvent to obtain desirable sedimentation behavior and/or diffusion behavior of the solute within the tube during centrifuge operations. In one embodiment, the angular velocity is maintained at a near-maximum value until just before precipitation of a solute component is reached within the tube. The tube angular velocity is then reduced as a function of time so that critical precipitation is approached but never occurs in the tube as the centrifuge process continues. In other embodiments, the net flux of solute particles into a given volume element of the centrifuge tube, or the ratio of net fluxes of two or more solutes into a predetermined volume elements, is caused to be a prescribed function of time. One application of this method is minimization of the time required to obtain a desired density gradient separation by a centrifuge process.

28 Claims, 3 Drawing Sheets

OPTIMAL CENTRIFUGAL SEPARATION

This is a continuation of application Ser. No. 07/492,709, filed Mar. 12, 1990 now abandoned.

BACKGROUND OF THE INVENTION

1. Field of the Invention

The present invention relates to centrifugation and more particularly to the control of rotor speed for controlling concentration variation in a centrifuge chamber.

2. Description of Related Art

Essentially, centrifugation is a process for separating particles suspended in a solution. In biological applications, the particles are usually macromolecules, cells, DNA fragments, etc. There are two primary types of centrifuge procedures, one being "preparative" which is to isolate specific particles, and the other being "analytical" which involves measuring the physical properties of a sedimenting particle.

The device used for centrifugation is a centrifuge which includes a rotor that supports several containers or centrifuge tubes, of sample solution for rotation about a common spin axis. As the rotor spins in the centrifuge, centrifugal force is applied to each particle in the sample solution; each particle will sediment at a rate which is proportional to the centrifugal force applied. The viscosity of the sample solution and the physical properties of the particle also affect the sedimentation rate of each individual particle. For a given centrifugal force, density and liquid viscosity, the sedimentation rate of the particle is proportional to its size (molecular weight), and to the difference between its density and the density of the solution.

One of many methods of centrifugal separation is differential centrifugation, or pelleting. In this method, the centrifuge tube is filled initially with a uniform mixture of sample solution. Through centrifugation, one obtains a separation of two fractions including a pellet containing the sedimented material, and supernatant solution of the unsedimented material. The pellet is a mixture of all of the sedimented components.

Another method of separation is by density gradient centrifugation, a method somewhat more complicated than differential centrifugation, but one which has compensating advantages. Not only does the density gradient method permit the complete separation of several or all of the components in a mixture according to their densities but, it also permits analytical measurements to be made. The density gradient method involves a supporting column of "density gradient" fluid whose density increases toward the bottom of the tube. The density gradient fluid consists of a suitable low molecular weight solute in a solvent in which the sample particles can be suspended.

There are two widely used methods of density gradient centrifugation: rate zonal and isopycnic. In the rate zonal technique, a sample solution containing particles to be separated is layered on a preformed gradient column. Under centrifugal force, the particles will begin sedimenting through the gradient toward the bottom of the centrifuge tube and separate into zones along the tube, each zone consisting of particles characterized by their sedimentation rate. The zones continue to move down the tube with time. To achieve a rate zonal separation, the density of the sample particles must be greater than the density at any specific position along the gradient column, in order for the particles to be able to continue to move down the tube. The run must be terminated before any of the separated zones reaches the bottom of the tube. Otherwise, two or more separated zones will mix at the bottom of the tube.

In the isopycnic technique, the density gradient column encompasses the whole range of densities of the sample particles. Each particle will sediment or float toward a position in the centrifuge tube at which the gradient density is equal to its own density, and there it will remain in equilibrium. The isopycnic technique, therefore, separates particles into zones on the basis of their density differences.

Density gradients can be formed manually by layering density gradient material of gradually decreasing densities in the centrifuge tube. In the isopycnic procedure, it is sometimes easier to start with a uniform solution of the sample and the gradient material. Under the influence of centrifugal force, the gradient material redistributes in the tube so as to form the required concentration (and density) gradient. This is often referred to as the selfgenerating gradient technique in which a continuous density gradient is formed when the diffusion of the gradient material towards the rotor spin axis balances the sedimentation away from the spin axis at each radial location along the centrifuge tube. Meanwhile, sample particles, which are initially distributed throughout the tube, sediment or float to their isopycnic positions. This self-generating gradient technique often requires long hours of centrifugation.

Generally, centrifugal separation can be effected in less time by centrifuging at higher rotor angular velocity. However, it is limited by the condition that the centrifugal force of the mass of the rotor and its contents at high rotor velocity not exceed the yield stress of the rotor. Furthermore, the rotor angular velocity is also limited by the condition that the solution of the gradient material not attain saturation at the outermost location of the centrifuge tube at any time during centrifugation. This is to avoid the possibility of salt crystallization or precipitation, which involves a process of accumulation of mass as the salt transforms from the dissolved to solid crystalline phase. This can lead to possible rotor failure due to excessive stress on the rotor by the dense crystalline salt.

Rotor manufacturers typically provide manuals that contain information regarding the top speed at which the rotor can be safely run for an indefinite period of time, for a given loading concentration, without reaching the gradient salt precipitation threshold. Referring to FIG. 1, $W_p$ represents the speed at which precipitation will never occur for an indefinite period of time for a particular loading density. In the past, centrifugation run has been carried out at a single speed $W_p$ to safely operate within the precipitation threshold (line 12). A more efficient method would be to run the rotor at the highest speed $W_y$ within the yield stress limit of the rotor, until precipitation is expected to occur at time $T_c$ at which time the rotor speed is reduced to the value $W_p$ which would then not allow precipitation to occur for an indefinite length of time (line 14). Using this method, the total elapsed centrifugation time required for a particular state of separation is less than that in the case of the single speed run. One can also compare the efficiency of the two methods by comparing the integrals of $W^2$ under the operating lines 12 and 14, the larger integral for the same elapsed time being representative of a more efficient centrifugation.

Recently, a new technique was proposed by Chulay et al in U.S. Pat. No. 4,941,868 which utilizes a dynamic simulation of gradient salt sedimentation to predict the elapsed time at which the precipitation threshold is reached for a number of discrete speeds. The technique requires several speed reductions in coarse steps (line 16) during a run to maintain the gradient salt density within the precipitation threshold. The reduced speeds are designated by the manufacturer and are selected via trial and error to decrease run time. This technique significantly increases the average speed of the rotor above that found in both of the previously described techniques. The amount of time required to attain separation is therefore substantially decreased.

While the technique described in the Chulay et al patent has been found to be efficient, the process for finding curve 16 is not automated; furthermore the rotor speed has not been optimized to produce the shortest run time. In recent days when centrifugation has quite a few competing technologies for macromolecular separation, automated minimization of the amount of time required for centrifugal separations has become commercially important. Because the technique described in the Chulay et al. patent requires a trial and error approach to selecting the speeds at which centrifugation is to be run, the highest possible speed at a particular elapsed time very often has not been selected.

SUMMARY OF THE INVENTION

The present invention is directed to a method of controlling the rotor speed for centrifugation in accordance with a user specified sedimentation and diffusion to obtain the desired concentration variation in the centrifuge chamber. The rotor speed is automatically controlled to vary practically continuously with time in the method.

In one aspect of the present invention, the method can be utilized to absolutely minimize the total amount of time for the separation of macromolecules in a density gradient forming solution. The maximum rotor speed is maintained throughout the centrifugation run subject to a rotor stress constraint on the concentration of the density gradient solution at the outermost location of the sample chamber in the rotor.

Other applications of the method include control of movements of macromolecules by varying rotor speed to obtain a desired time dependent concentration, and control of movements of two or more species by varying rotor speed to obtain a desired concentration ratio between the species at a desired radial location.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

One aspect of the present invention is a method which absolutely minimizes centrifugation time within the constraint of salt crystallization or precipitation in, for example, a cesium chloride ("CsCl") self-forming density gradient solution. It will be appreciated that the present invention can be practiced with other types of gradient solutions and in other applications such as rate zonal separation. To simplify the description of the present invention, the centrifuge tube used is a cylindrical test tube oriented with its axis horizontal during centrifugation. The analysis below can be applied to other types of centrifuge tubes of different geometry and orientation and other types of rotors.

Figure 1:
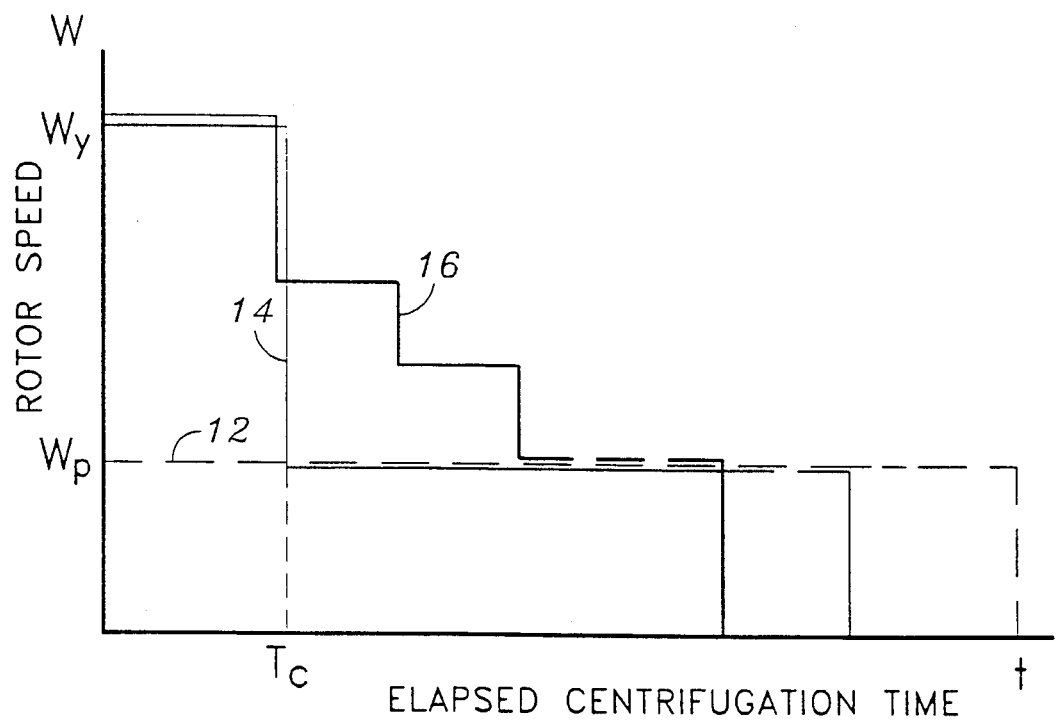
FIG. 1 is a graph showing the rotor speed vs. time of prior art centrifugation methods.
Figure 2:
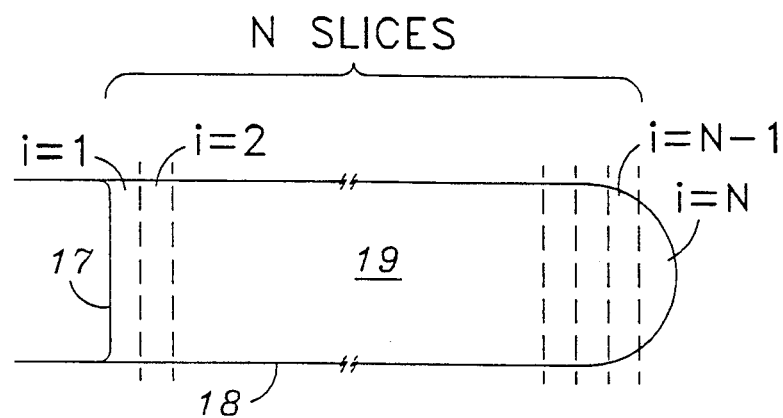
FIG. 2 is a diagram illustrating the mathematical division of a centrifuge tube to aid in the description of the numerical analysis of the present invention.

Referring to FIG. 2, the solution 19 in the centrifuge tube 18 is divided into N slices beginning from the meniscus 17 of the solution. N can be any integer number, the value of which will determine the accuracy of the calculation and the computation time required. Each slice has a finite thickness and volume and is separated from adjacent slices by imaginary boundaries. The governing equation for sedimentation and diffusion is a well known precursor of the Lamm equation:

$$J_{i-1,i} = sW^2 r_{i-1,i} \overline{C_{i-1,i}} - D\Delta C_{i-1,i}$$

where $i=1, ..., N$; $J_{i-1,i}$ is the flux, or time rate of passage of particles per unit area across the boundary separating the $(i-1)$th and $i$th slices; $s$ is the sedimentation coefficient of the particles; $W$ is the angular velocity of the rotor; $r_{i-1,i}$ is the radial distance of the boundary separating the $(i-1)$th and $i$th slices measured from the axis of rotation; $\overline{C_{i-1,i}}$ is the average concentration of particles in the $(i-1)$th and $i$th slices (expressed as number of particles per unit volume); $D$ is the diffusion coefficient for the particles which depends on the size and shape of the particles, the viscosity of the solution and temperature; and $\Delta C_{i-1,i}$ is the "gradient" of the concentration of particles at $r_{i-1,i}$.

Figure 3:
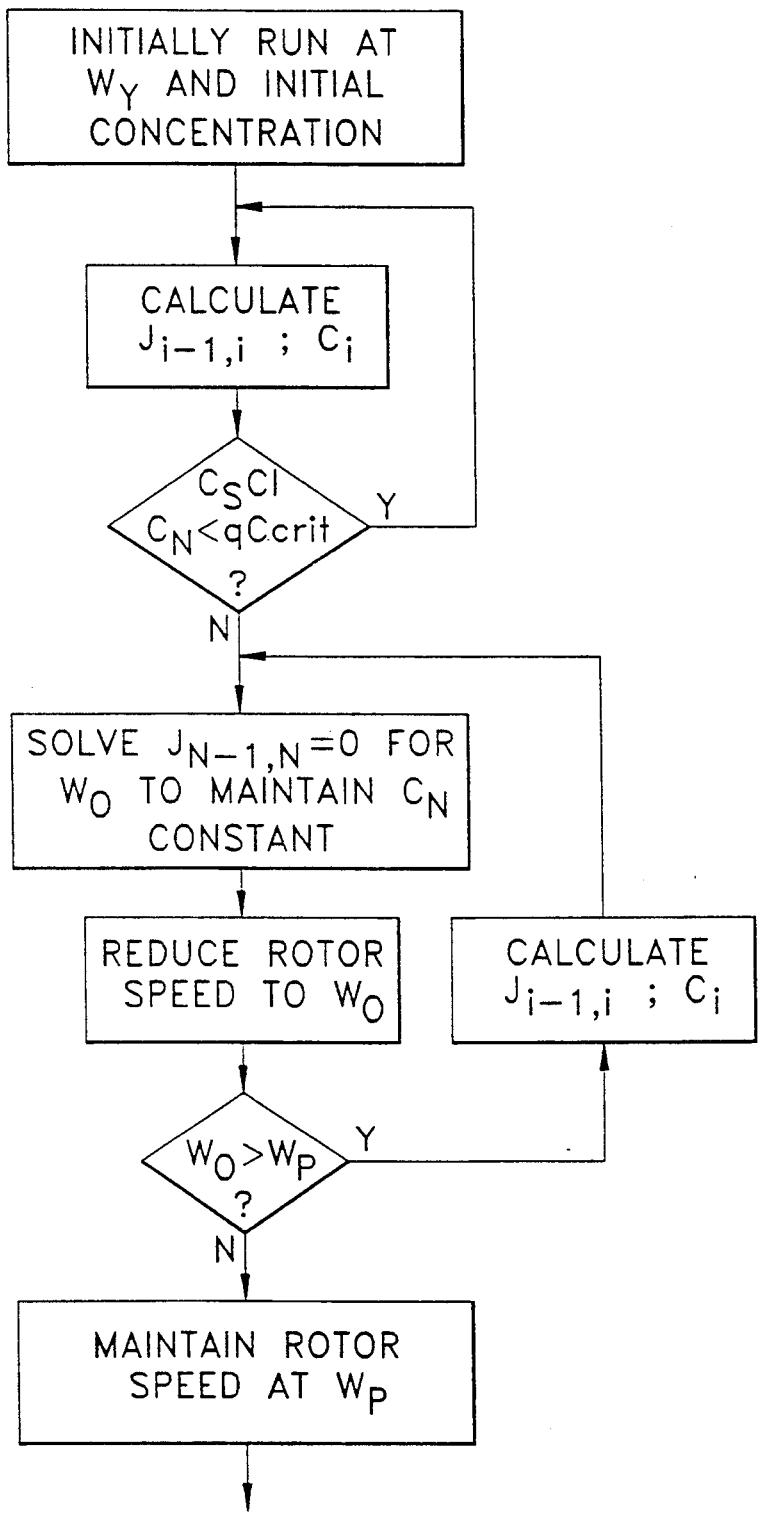
FIG. 3 is a flowchart of rotor speed control in accordance with one aspect of the present invention.
Figure 4:
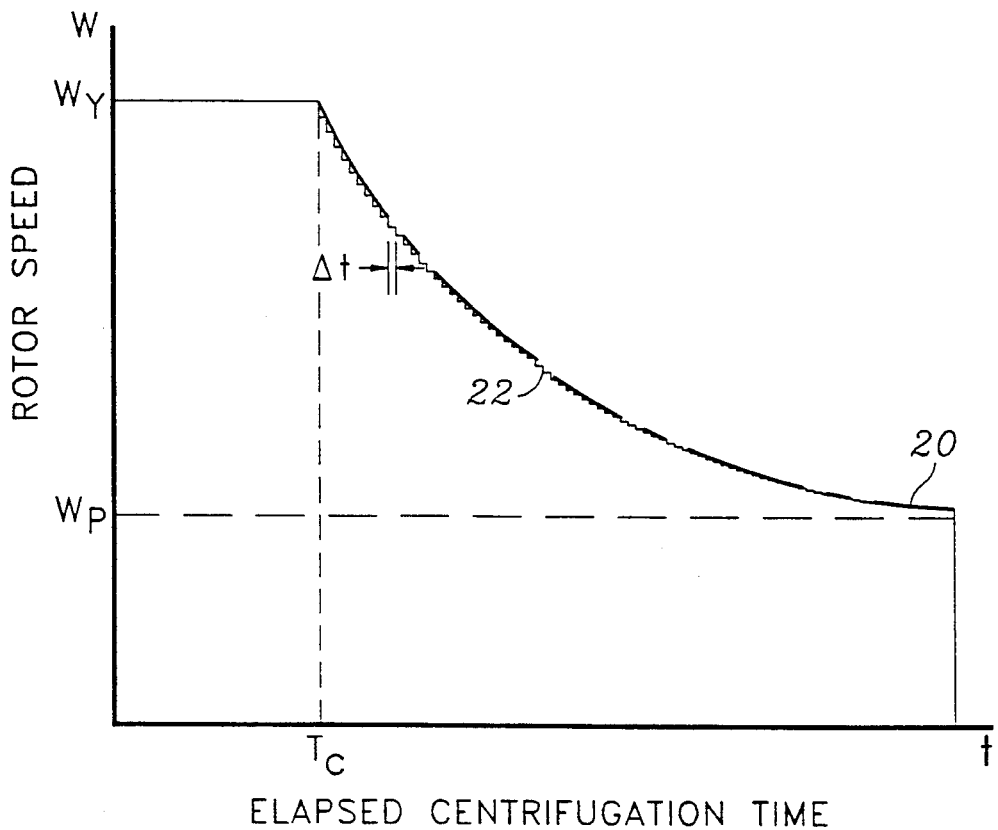
FIG. 4 is a graph showing rotor speed vs. time of rotor speed control in accordance with one aspect of the present invention.

Referring to FIGS. 3 and 4 the method for the determination of the optimal rotor speed that will result in the shortest amount of time required for density gradient separations is first outlined. Centrifugation is started at the maximum speed $W_y$ permissible for the particular rotor and average density of the solution. The maximum speed $W_y$ is determined from rotor yield stress specifications provided by the rotor manufacturers. Centrifugation is continued at that speed until the time $t=T_c$ when the concentration $C_N$ of the gradient salt, e.g. CsCl, in the bottom of the tube reaches the critical precipitation threshold value $C_{crit}$ or a value within a desired margin of safety ($q \times C_{crit}$ where $0 < q < 1$, and in practice q is close to 1). The speed $W_o$ that is required to make the flux $J_{N-1,N}$ into the bottom (Nth) slice equal to exactly zero is then calculated. The rotor speed is then reduced to this new speed $W_o$ thereby keeping the concentration in the bottom slice $C_N$ at or below (close to) the critical precipitation threshold value $C_{crit}$. At each iteration the rotor speed is similarly calculated and reduced so as to maintain the concentration $C_N$ in the bottom slice at or below (close to) precipitation concentration $C_{crit}$ or $q \times C_{crit}$ for all times after $T_ct > Tc$. The change in rotor speed with time required to maintain close to critical concentration is best illustrated by line 22 in FIG. 4. The rotor speed is maintained as close as is practical to the critical speed limit; higher speeds would cause precipitation of the gradient material. The smoothness of the curve 22 will depend on the frequency of successive iterations In theory, a smooth line 20 can be obtained using a large N value and high speed processors.

The premise of this particular aspect of the present invention is based on the observation that after the Nth slice reaches the critical concentration $C_{crit}$ or $q \times C_{crit}$ at $t = T_c$, if the rotor speed is controlled such that the net flux of gradient salt into this slice is zero, then the concentration of the gradient salt at the bottom of the tube cannot ever change after $t = T_c$. Centrifugation can thus be carried out at the highest speeds (shortest time) without fear of precipitation problems.

The steps for obtaining concentration and rotor speed values will now be described in detail. The computer algorithm associated with these steps, however, will not be described since it is merely an exercise of computational programming skills involving conventional numerical computation techniques. The entire U.S. Pat. No. 4,941,868 is incorporated by reference herein to illustrate the state of the art of transient analysis of centrifugal separation.

Given the initial concentrations in each slice, the initial rotor speed $W_y$ consistent with rotor yield stress constraint for the particular average fluid density, and the diffusion and sedimentation constants, the flux $J_{i-1,i}$ across each boundary at each distance $r_{i-1,i}$ can be calculated. As is consistent with finite difference approximation, $\Delta C_{i-1,i}$ is approximated as the difference of the concentrations $(C_{i-1}, C_i)$ across adjacent slices divided by a distance measured between the centers of the slices, which in the case of slices of equal thickness equals the thickness of a slice. For initial concentrations in each slice, the simplest example will be the case where the concentrations are the same for each slice as in the case of a homogenous self-forming density gradient solution, e.g. cesium chloride.

The total number of particles that travel across each boundary during the period $\Delta t$ is then simply given by:

$$J_{i-1,i} A_{i-1,i} \Delta t$$

where $A_{i-1,i}$ is the area of the boundary between the $(i-1)$th and ith slices. In the case of the test tube in the example shown in FIG. 2, this area will be the same for all boundaries except for the slices near the bottom of the tube. The total number of particles residing in a particular slice after period $\Delta t$ will be given by {the number of particles originally present} plus {the net number of particles flowing into that slice}. Since the geometry and thus the volume of the slice is known, the new concentration $C_i$ after period $\Delta t$ is given by the total number of particles in the slice divided by the slice volume.

By obtaining the flux at each and every one of the boundaries and subsequently applying the just described steps for calculating the concentrations, one can obtain the new concentration values at any time t, thereby modeling the concentrations of the particles.

The same calculations are repeated after each period $\Delta t$. Each iteration, the concentration values $C_i$ obtained for the preceding $\Delta t$ period are used to obtain the flux values for the current $\Delta t$ period, which in turn are used to obtain a new set of concentration values. This iterative process continues indefinitely until a user specified condition has been met.

For purposes of controlling rotor speed to avoid precipitation of gradient-forming salt, the condition specified is that the concentration in the Nth slice should be less than the concentration at which the density gradient solution will precipitate, and preferably within a margin of safety q. Once this condition has been met at $t = T_c$, the next iteration at $T_c + \Delta t$ requires that the flux $J_{N-1,N}$ into the Nth slice is set to equal exactly zero. One thus solves for $W_o$, a unique rotor speed which will satisfy $J = 0$. In particular, the following equation for the rotor speed, $W_o$, is solved:

$$J_{N-1,N} = sW_o^2 r_{N-1,N} \overline{C_{N-1,N}} - D (C_{N-1} - C_N)/\Delta r = 0$$

where $J_{-1,N}$ = the flux through the boundary separating the $(N-1)$th and Nth slices; $W_o$ = the rotor speed which satisfies the zero flux condition; $C_{N-1}, C_N$ = the concentration of the gradient salt in the $(N-1)$th and Nth slices, respectively (note that $C_N = q\ C_{crit}$ in the Nth slice); $\overline{C_{N-1,N}}$ = average concentration in the $(N-1)$th and Nth slices; $r_{N-1,N}$ = the radial distance of the boundary separating the $(N-1)$th and Nth slices measured from the axis of rotation; $\Delta r$ = distance between midlines of the $(N-1)$th and Nth slices.

The rotor is slowed down to the new speed $W_o$. As before, the new fluxes and concentration values for all the slices are next calculated, based this time on the new speed value found from $J = 0$. Thereafter for each iteration a new rotor speed is calculated. Theoretically, the rotor speed should change (decrease) at each iteration following the first instance at $t = T_c$ when the critical concentration criterion $C_{crit}$ has been met, until $W_p$ (the speed at which precipitation will never occur for an indefinite period of time) has been asymptotically approached. It is understood that the process may be terminated at any time before or after $W_p$ has been reached in accordance with a user specified condition, e.g. a specified elapsed run time.

It can be appreciated that the method of the present invention provides complete automation in optimizing centrifugation (at absolute minimum operating time). The optimized time dependent rotor speed may be predicted through computer simulation and programmed into the control systems of centrifuges which runs on variable speed motors, for example, the Optima ™ series ultracentrifuges developed and manufactured by Beckman Instruments, Inc. The line 22 in FIG. 4 may be approximated by line 20 which can be expressed as an analytical equation and programmed into the control system of the centrifuge to provide a fine control of the rotor speed. Alternatively, the centrifuge may be controlled under "real-time" calculation of the rotor speed. Depending on the resolution of the motor speed control, centrifugation can be carried out close to the optimum conditions represented by line 20 in FIG. 4.

Figure 5:
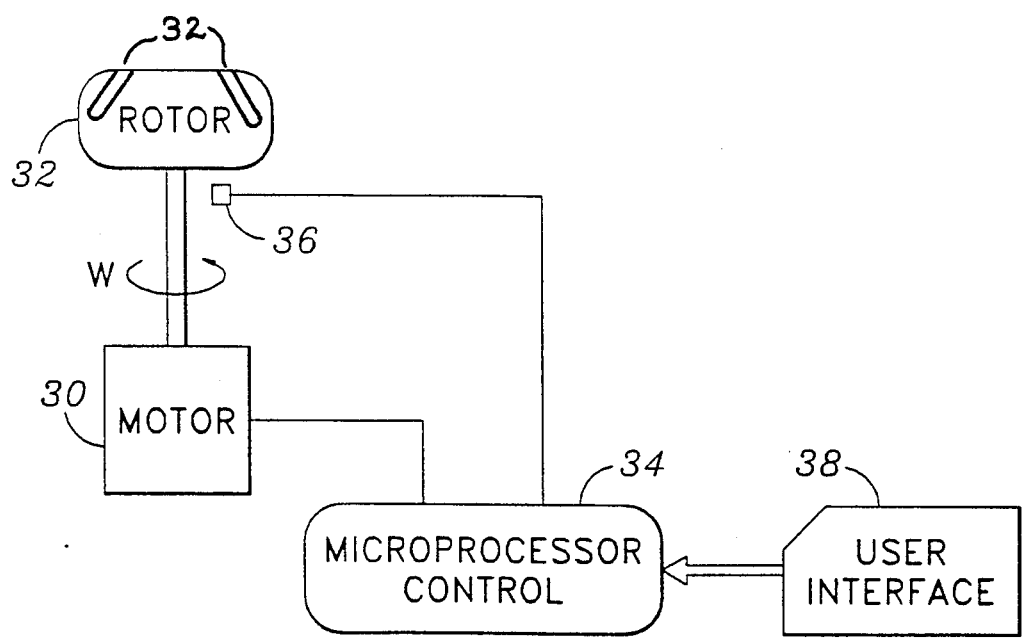
FIG. 5 is a schematic diagram of a rotor and speed controller.

A schematic diagram of the control system of the centrifuge is shown in FIG. 5. A variable speed motor 30 drives the rotor 32 which supports centrifuge tubes 33 containing samples for rotation within the chassis (not shown) of the centrifuge. The speed of the motor 30 is controlled by a microprocessor controller 34 in accordance with the technique heretofore described. A speed sensor 36 provides feedback of the rotor speed to the controller 34. Relevant input data such as initial concentration profile, constants and tube geometry are input through user interface 38.

The present invention is not limited to a particular type of rotor or centrifuge tube. Any combination of rotor, centrifuge tube, loading configuration of the density gradient solution can be simulated and controlled using the method of the present invention.

The thickness and the boundary area may be different for each slice for tubes with special geometry. To improve the resolution and accuracy of the process, the time interval $\Delta t$ between each iteration may be different for different rotors and/or different time segments in the process; for example it is preferred to have very small time intervals for the first few iterations to avoid singularities in the numerical integration.

It is noted that in the foregoing description of the method, the flux analysis begins at a given initial rotor speed. In an actual centrifugation run, however the rotor speeds up from rest to such "initial speed". However, the time taken to do this is negligible compared to the total run time and the transient sedimentation and diffusion flows during this start-up period is negligible. The start-up period therefore can be ignored to a good approximation. One can of course include flux analysis of the start-up period for marginal improvement in precision.

Using similar flux analysis as described above, it is possible to specify the condition that the concentration of a component of the sample solution in any slice should vary as a specified function of time f(t) where $$(\text{slice volume}) \times \frac{dC_i}{dt} = J_{i-1,i}A_{i-1,i} - J_{i,i+1}A_{i,i+1} = f(t).$$

This might be useful for example in analytical centrifugation in which the sample solution in the centrifuge chamber is observed during centrifugation to studying its sedimentation behavior. Another application of the present invention is to control the ratio of the influx of two or more macromolecules, e.g. DNA particles types A and B, at a particular radial location in the centrifuge tube. The ratio of concentrations of the macromolecules can be specified to vary as a function of time:

$$\frac{\Delta[C_i]_A}{\Delta[C_i]_B} = \frac{[J_{i-1,i}A_{i-1,i} - J_{i,i+1}A_{i,i+1}]_A}{[J_{i-1,i}A_{i-1,i} - J_{i,i+1}A_{i,i+1}]_B} = f(t).$$

Both of the above applications are implemented by varying the rotor speed with time. Instead of solving for $J_{N-1,N}=0$ for $W_o$ as in the control of critical concentration described earlier, the solutions of the flux equations yield rotor speeds that satisfy the specified f(t).

While the invention has been described with respect to the preferred embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

I claim:

1. A method of centrifuging a sample solution comprising the steps of:

supporting a sample solution in a rotor of a centrifuge, said sample solution having at least one solute component therein, rotating said sample solution in said rotor at a timedependent variable rotation speed W about a rotation axis, said rotating sample solution characterized by a sedimentation and diffusion behavior of said solute component that is a function of rotation speed and time, said sedimentation and diffusion behavior including time-dependent concentrations $C_i$ (i=1,2, ..., N) of the solute component at radial positions $r_i$ in said sample solution relative to said rotation axis and time-dependent flux $J_{i,i+1}$ of said solute component from each said radial position $r_i$ to a radially adjacent position $r_{i+1}$ in said sample solution, specifying a set of conditions on said sedimentation and diffusion behavior which are to be satisfied, said set of conditions including at least one condition on one of said concentrations and flux of said solute component which is to be satisfied at least one radial position in said sample solution in order to avoid precipitation of said solute component from said sample solution, simulating said sedimentation and diffusion behavior of said solute component of said sample solution as a function of rotation speed and time, said simulating including computing, in each of a plurality of successive time intervals, the flux $J_{i,i+1}$ as a function of rotation speed W of said solute component during that time interval between each pair of radially adjacent positions $r_i$ and $r_{i+1}$ in said sample solution, and the corresponding concentration $C_i$ of said solute component during the next successive time interval at each radial position $r_i$ in said sample solution that results from said flux, determining, in each of said plurality of successive time intervals, from said simulated sedimentation and diffusion behavior, a maximum rotation speed during said time interval that satisfies said specified set of conditions, and adjusting said time-dependent variable rotation speed to substantially equal to the latest maximum rotation speed that has been determined.

2. The method of claim 1 wherein said set of conditions includes a concentration-independent condition that said rotation speed W have an upper limit for which a yield stress limit of said rotor is not exceeded.

3. The method of claim 1 wherein said at least one condition is that for i=k the concentration $C_k$ of said solute component at a specified radial position $r_k$ in said sample solution relative to said rotating axis vary according to a particular specified function of time f(t).

4. The method of claim 3 wherein i=k=N, where $r_n$ is a position in said sample solution furthest from said rotation axis.

5. The method of claim 4 wherein for i=N the concentration $C_n$, defined by said function f(t), increases for time $0<t<T_c$ until said concentration $C_N$ reaches a value of $q \times C_{crit}$ in a time interval $T_c$, where q is a specified safety margin with $0<q\leq 1$ and $C_{crit}$ is a critical concentration at which said solute component precipitates from said sample solution, and wherein said concentration $C_N$ is substantially constant at $q \times C_{crit}$ for time intervals $t>T_c$, whereby said solute component is prevented from precipitating.

6. The method of claim 1 wherein said at least one condition is that for i=k the flux $J_{k-1,k}$ of said solute component from a specified radial position $r_{k-1}$ to a radially adjacent position $r_k$ in said sample solution vary according to a particular function of time $f(t)$.

7. The method of claim 6 wherein $i=k=N$ where $r_N$ is the position in said sample solution furthest from said rotation axis.

8. The method of claim 7 wherein for $i=N$ the flux $J_{N-1,N}$, defined by said function $f(t)$, is substantially zero for time $t>T_c$ after a time interval $T_c$ in which the concentration $C_N$ of said solute component at said specified position $r_N$ reaches a value of $q \times C_{crit}$, where q is a specified safety margin with $0<q\leq 1$ and $C_{crit}$ is a critical concentration at which said solute component precipitates from said sample solution.

9. A method of centrifuging comprising the steps of:
providing a solute and a solvent in a centrifuge tube that has a rotation axis and a rotor mechanism;
dividing, for computational purposes, the contents of the centrifuge tube into a plurality of volume elements $\Delta V_i (i=1, 2, \ldots, N$, where $N>3)$, with each volume element $\Delta V_i$ being approximately a fixed radial distance $r=r_i$ from the rotation axis, where at least one volume element $\Delta V_N$ has the largest associated radial distance $r=r_N$ from the rotation axis;
rotating the centrifuge tube about its rotation axis at an angular velocity $W=W(t)$ as a function of time t to produce a flux $J_{i,i+1}(t)$ of solute particles between adjacent volume elements $\Delta V_i$ and $\Delta V_n$ so that concentration $C_i(t)$ of solute in a volume element $\Delta V_i$ varies with time; and
determining and automatically adjusting the angular velocity $W(t)$ approximately continuously as a function of time t so that $C_N(t)$ of the solute in the volume element $\Delta V_N$, computed using the angular velocity $W(t)$ for rotation of the centrifuge tubes, increases with time to a predetermined critical $C_{crit}$ at a determinable time $t=T_c$ and does not increase above the value $C_{crit}$ for any time t greater than $T_c$.

10. The method of claim 9, further comprising the step of causing said angular velocity $W(t)$ to have an initial value that is less than, but approximately equal to, the maximum angular velocity $W=W_{max}$ permitted to preserve the structural integrity of said rotor mechanism.

11. The method of claim 10, further comprising the step of holding said angular velocity $W(t)$ approximately constant at $W(t)=W_{max}$ for all times t up to said time $t=T_c$.

12. A method of centrifuging comprising the steps of:
providing a solute and a solvent in a centrifuge tube that has a rotation axis and has a rotor mechanism;
dividing, for computational purposes, the contents of the centrifuge tube into a plurality of volume elements $\Delta V_i(i=1,2, \ldots, N$, where $N>3)$, with each volume element $\Delta V_i$ being approximately a fixed radial distance $r=r_i$ from the rotation axis, where at least one volume element $\Delta V_N$ has the largest associated radial distance $r=r_N$ from the rotation axis;
rotating the centrifuge tube about its rotation axis at an angular velocity $W=W(t)$ as a function of time t to produce a flux $J_{i-1,i}(t)$ of solute particles between adjacent volume elements $\Delta V_{i-1}$ and $\Delta V_i$ and a flux $J_{i,i+1}(t)$ of solute particles between adjacent volume elements $\Delta V_i$ and $\Delta V_{i+1}$ so that concentration $C_i(t)$ of solute in a volume element $\Delta V_i$ varies with time; and
determining and automatically adjusting the angular velocity $W(t)$ approximately continuously as a function of time t so that the net flux of solute particles into the volume element $\Delta V_i$, computed using the angular velocity $W(t)$ for rotation of the centrifuge tube, varies with time as a predetermined function $f(t)$ of time.

13. The method of claim 12, further comprising the step of causing said angular velocity $W(t)$ to have an initial value $W_O$ that is less than, but approximately equal to, the maximum angular velocity $W=W_{max}$ permitted to preserve the structural integrity of said rotor mechanism.

14. The method of claim 13, further comprising the step of holding said angular velocity $W(t)$ approximately constant at $W(t)=W_{max}$ for all times t up to a predetermined time $t=T_c$.

15. A method of centrifuging comprising the steps of:
providing first and second solutes and a solvent in a centrifuge tube that has a rotation axis and has a rotor mechanism;
dividing, for computational purposes, the contents of the centrifuge tube into a plurality of volume elements $\Delta V_i(i=1, 2, \ldots, N$, where $N>3)$, with each volume element $\Delta V_i$ being approximately a fixed radial distance $r=r_i$ from the spin axis, where at least one volume element $\Delta V_N$ has the largest associated radial distance $r=r_N$ from the rotation axis;
rotating the centrifuge tube about its rotation axis at an angular velocity $W=W(t)$ as a function of time t to produce a net flux $J_i(t)_A$ of first solute particles A into a predetermined volume element $\Delta V_i$; and a net flux $J_i(t)_B$ of second solute particles B into the same volume element; and
determining and automatically adjusting the angular velocity $W(t)$ approximately continuously as a function of time t so that the ratio of the net flux $J_i(t)_A$ of solute particles to the net flux $J_i(t)_B$ of solute particles into the predetermined volume element computed using the angular velocity $W(t)$ for rotation of the centrifuge tube, varies with time as a predetermined function $f(t)$ of time.

16. The method of claim 15, further comprising the step of causing said angular velocity $W(t)$ to have an initial value that is less than, but approximately equal to, the maximum angular velocity $W=W_{max}$ permitted to preserve the structural integrity of said rotor mechanism.

17. The method of claim 16, further comprising the step of holding said angular velocity $W(t)$ approximately constant at $W(t)=W_{max}$ for all times t up to a predetermined time $t=T_c$.

18. Centrifuge apparatus comprising:
a rotor, having a rotation axis, for receiving and holding a sample solution that includes a solvent and a solute and for rotating of the sample solution about the rotation axis, the rotor having at least one volume element $\Delta V_N$ containing sample solution whose radial distance $r_N$ from the rotation axis is at least as large as the radial distance $r_i$ from the rotation axis of any other volume element $\Delta V_i$ ($i=1,2, \ldots, N$) of the rotor;
rotor drive means, connected to the rotor, for rotating the rotor about the rotation axis with a time varying angular velocity $W=W(t)$ to produce a flux of solute particles between different portions of the rotor; and control means, connected to the rotor drive means, for determining and automatically adjusting the angular velocity W(t) approximately continuously as a function of time t so that concentration $C_N$ of solute particles in the volume element $\Delta V_N$ increases with time to a predetermined $C_{crit}$ at a determinable time $t=T_c$ and does not increase above the value $C_{crit}$ for any time greater than $T_c$.

19. The apparatus of claim 18, wherein said control means causes said angular velocity W(t) to have an initial value that is less than, but approximately equal to, the maximum angular velocity $W=W_{max}$ permitted to preserve the structural integrity of said rotor mechanism.

20. The apparatus of claim 19, wherein said control means causes said angular velocity W(t) to be approximately constant at $W(t)=W_{max}$ for all times t up to said time $t=T_c$.

21. Centrifuge apparatus comprising:
a rotor, having a rotation axis, for receiving and holding a sample solution that includes a solvent and a solute and for rotating of the sample solution about the rotation axis, the rotor having at least one volume element $\Delta V_N$ containing sample solution whose radial distance $r_N$ from the rotation axis is at least as large as the radial distance $r_i$ from the rotation axis of any other volume element $\Delta V_i(i=,2,\ldots,N)$ of the rotor;
rotor drive means, connected to the rotor, for rotating the rotor about the rotation axis with a time varying angular velocity $W=W(t)$ to produce a flux of solute particles between different portions of the rotor; and
control means, connected to the rotor drive means, for automatically adjusting the angular velocity W(t) approximately continuously as a function of time t so that the net flux $J_i$ of solute particles into the volume element $\Delta V_i$ varies with time as a predetermined function of time f(t).

22. The apparatus of claim 21, wherein said control means causes said angular velocity W(t) to have an initial value $W_O$ that is less than, but approximately equal to, the maximum angular velocity $W=W_{max}$ permitted to preserve the structural integrity of said rotor mechanism.

23. The apparatus of claim 22, wherein said control means causes said angular velocity W(t) to be approximately constant at $W(t)=W_{max}$ for all times t up to a predetermined time $t=T_c$.

24. Centrifuge apparatus comprising:
a rotor, having a rotation axis, for receiving and holding a sample solution that includes a solvent and first and second solutes and for rotating of the sample solution about the rotation axis, the rotor having a plurality of volume elements $\Delta V_i(i=1,2,\ldots,N)$ at various radial volume element $\Delta V_N$ containing a sample solution whose radial distance $r_N$ from the rotation axis is at least as large as the radial distance $r_i$ from the rotation axis of any other volume element of the rotor;
rotor drive means, connected to the rotor, for rotating the rotor about the rotation axis with a time varying angular velocity $W=W(t)$ to produce a flux of solute particles between radially different portions of the rotor; and
control means, connected to the rotor drive means, for automatically adjusting the angular velocity W(t) approximately continuously as a function of time t so that the ratio of the net flux of first solute particles into a predetermined volume element $\Delta V_i$ to the net flux of second solute particles into the same predetermined volume element varies with time as a predetermined function of time f(t).

25. The apparatus of claim 24, wherein said control means causes said angular velocity W(t) to have an initial value $W_O$ that is less than, but approximately equal to, the maximum angular velocity $W=W_{max}$ permitted to preserve the structural integrity of said rotor mechanism.

26. The apparatus of claim 25, wherein said control means causes said angular velocity W(t) to be approximately constant at $W(t)=W_{max}$ for all times t up to a predetermined time $t=T_c$.

27. A centrifuge apparatus comprising:
means for supporting a sample solution for rotation about a rotation axis, said sample solution having at least one solute component therein;
means for rotating said sample solution at a timedependent variable rotation speed about the rotation axis, said rotated sample solution characterized by a sedimentation and diffusion behavior of said solute component that is a function of rotation speed, time and radial position in said sample solution relative to said rotation axis;
means for obtaining said time-dependent variable rotation speed including:
means for specifying a condition on said sedimentation and diffusion behavior which are to be satisfied;
means for simulating said sedimentation and diffusion behavior of said solute component as a function of rotation speed and time in a plurality of successive time intervals; and
means for determining from said simulated sedimentation and diffusion behavior a rotation speed during each of said plurality of successive time intervals that satisfied said specified condition thereby obtaining said time-dependent variable rotation speed.

28. A method of centrifuging a sample solution comprising the steps of:
supporting a sample solution in a centrifuge, said sample solution having at least one solute component therein;
centrifuging said sample solution at a time-dependent variable rotation speed about a rotation axis, said centrifuging sample solution characterized by a sedimentation and diffusion behavior of said solute component that is a function of rotation speed, time and radial position in said sample solution relative to said rotation axis;
whereby said time-dependent variable rotation speed is obtained by:
specifying a condition on said sedimentation and diffusion behavior which are to be satisfied;
simulating said sedimentation and diffusion behavior of said solute component as a function of rotation speed and time for a plurality of successive time intervals; and
determining from said simulated sedimentation and diffusion behavior in each of said plurality of successive time intervals, a rotation speed during each of said time intervals that satisfies said specified condition, thereby obtaining said time-dependent variable rotation speed.

* * * * *

UNITED STATES PATENT AND TRADEMARK OFFICE
CERTIFICATE OF CORRECTION

PATENT NO. : 5,171,206
DATED : December 15, 1992
INVENTOR(S) : Jeffrey J. Marque It is certified that error appears in the above-identified patent and that said Letters Patent is hereby corrected as shown below:

Column 11, line 27    after "(i =" insert --1--

Column 11, line 56    after "radial" insert --distances $r_i$ from the rotation axis, including at least one--

Signed and Sealed this

Twenty-third Day of November, 1993

Attest:

BRUCE LEHMAN

Attesting Officer    Commissioner of Patents and Trademarks